(12) United States Patent
Yip et al.

(10) Patent No.: US 6,950,607 B2
(45) Date of Patent: Sep. 27, 2005

(54) MULTI-FRAGRANCE SCENT DISPENSER

(75) Inventors: Po Chun Yip, Singapore (SG); Arnold Thaler, Weston, FL (US); Robert Fellows, Park Ridge, NJ (US)

(73) Assignee: Hometek International Ltd., Hong Kong (CN)

( * ) Notice: Subject to any disclaimer, the term of this patent is extended or adjusted under 35 U.S.C. 154(b) by 40 days.

(21) Appl. No.: 11/005,237

(22) Filed: Dec. 6, 2004

(65) Prior Publication Data

US 2005/0094988 A1 May 5, 2005

Related U.S. Application Data

(62) Division of application No. 10/427,434, filed on May 1, 2003, now Pat. No. 6,859,615.

(51) Int. Cl.[7] .................................................. F24F 6/08
(52) U.S. Cl. ...................................... 392/395; 392/390
(58) Field of Search .............................. 392/386, 390, 392/392, 393, 394, 395; 239/44, 45, 58, 59

(56) References Cited

U.S. PATENT DOCUMENTS

| | | | |
|---|---|---|---|
| 472,133 A | 4/1892 | Merrill | |
| 2,961,167 A | 11/1960 | Skaist | |
| 4,526,320 A | 7/1985 | von Philipp et al. | |
| 4,629,604 A | 12/1986 | Spector | |
| 4,968,487 A | * | 11/1990 | Yamamoto et al. ......... 422/125 |
| 5,038,394 A | * | 8/1991 | Hasegawa et al. .......... 392/395 |
| 5,111,477 A | | 5/1992 | Muderlak |
| 5,201,025 A | | 4/1993 | Landesberg |
| 5,259,062 A | | 11/1993 | Pelonis |
| 5,311,616 A | | 5/1994 | Pratt |
| 6,236,807 B1 | | 5/2001 | Ruffolo et al. |
| 6,278,840 B1 | | 8/2001 | Basaganas Millan |
| 6,285,830 B1 | | 9/2001 | Basaganas Millan |
| 6,374,045 B2 | | 4/2002 | Basaganas Millan |
| 6,411,776 B1 | | 6/2002 | Millan |
| 6,466,739 B2 | | 10/2002 | Ambrosi et al. |
| 6,487,367 B2 | | 11/2002 | Vieira |
| 6,659,301 B2 | * | 12/2003 | Fellows et al. ............. 215/400 |
| 2002/0066798 A1 | | 6/2002 | Laudamiel-Peliet |
| 2002/0146242 A1 | | 10/2002 | Vieira |

* cited by examiner

Primary Examiner—Sang Y. Paik
(74) Attorney, Agent, or Firm—Richard M. Goldberg

(57) ABSTRACT

A multi-fragrance scent dispenser includes a housing having an outlet opening; first and second holders in the housing for holding first and second liquid fragrance containers having first and second wicks, respectively, extending out of the first and second liquid fragrance containers; a first heater positioned in the housing to be in surrounding relation to the first wick when the first liquid fragrance container is held by the first holder; a second heater positioned in the housing to be in surrounding relation to the second wick when the first liquid fragrance container is held by the first holder; a control circuit which selectively controls activation of the first and second heaters; and a blocking plate movable relative to the heaters for at least partially blocking escape of evaporated fragrance through the outlet opening from at least one of the first and second wicks.

14 Claims, 18 Drawing Sheets

MULTI-FRAGRANCE SCENT DISPENSER

BACKGROUND OF THE INVENTION

The present invention relates generally to scent dispensers, and more particularly, is directed to a scent dispenser for emitting multiple fragrances.

Although air fresheners or scent dispensers which deliver scents to an enclosed area are well known, most of these scent dispensers only emit one type of fragrance. However, a user becomes accustomed to a particular scent over a period of time, and thereby loses any feeling for that particular scent. In other words, the user becomes so used to the scent that it is no longer noticeable to the user.

There are scent dispensers that can dispense multiple fragrances.

For example, U.S. Patent Publication No. 2002/0146242 to Vieira discloses a multiple-scent containing article formed by a flat circular cartridge with a plurality of scent elements around the periphery thereof, each containing a different scent. There is an opening so that only one scent element is exposed at a time, and a heater is positioned below the opening to heat the scent element and release the vapor. A fan flows the released vapor out of the cartridge. Alternatively, the disk can remain stationary and a plurality of heating elements could be provided. In addition, the device can be set for durations of time for each scent. However, there is no arrangement for partially blocking the heating effect to each scent element to adjust the amount of scent that is emitted.

As another example, U.S. Patent Publication No. 2002/0066798 to Laudamiel-Pellet et al discloses a multiple scent-containing article having a plurality of heating elements that lie under the scent-containing receptacles in which the device can be set for durations of time for each scent. However, again, there is no arrangement for partially blocking the heating effect to each scent element to adjust the amount of scent that is emitted.

OBJECTS AND SUMMARY OF THE INVENTION

Accordingly, it is an object of the present invention to provide a multi-fragrance scent dispenser that overcomes the problems with the aforementioned prior art.

It is another object of the present invention to provide a multi-fragrance scent dispenser that sequentially activates the heaters associated with different fragrance materials during predetermined time periods.

It is still another object of the present invention to provide a multi-fragrance scent dispenser in which the activation of the different heaters can be manually controlled.

It is yet another object of the present invention to provide a multi-fragrance scent dispenser in which the activation of the different heaters can be partially or wholly blocked to regulate the amount of scent for each fragrance.

It is a further object of the present invention to provide a multi-fragrance scent dispenser having adjustable holders which can hold different shape and dimension bottles such that the wick thereof is always at a desired position relative to the heater assemblies.

It is a still further object of the present invention to provide a multi-fragrance scent dispenser which can use gel packs positioned above the heater assemblies in combination with the bottles, or alternatively, the gel packs can be used in place of the fragrance containing bottles with wicks surrounded by the heater assemblies.

It is a yet further object of the present invention to provide a multi-fragrance scent dispenser having a fan for blowing the vaporized fragrance out of the second dispenser.

In accordance with an aspect of the present invention, a multi-fragrance scent dispenser includes a housing having an outlet opening; a first holder in the housing for holding a first liquid fragrance container having a first wick extending out of the first liquid fragrance container; and a second holder in the housing for holding a second liquid fragrance container having a second wick extending out of the second liquid fragrance container. A first heater is positioned in the housing to be in surrounding relation to the first wick when the first liquid fragrance container is held by the first holder, and a second heater is positioned in the housing to be in surrounding relation to the second wick when the first liquid fragrance container is held by the first holder. A control circuit selectively controls activation of the first and second heaters. Further, there is at least one blocking plate movable relative to the heaters for at least partially blocking escape of evaporated fragrance through the outlet opening from at least one of the first and second wicks.

The at least one blocking plate includes at least one opening for movement into and out of alignment with the first and second wicks for adjusting escape of the evaporated fragrance from the first and second wicks. The at least one blocking plate is positioned above the first and second wicks for slidable movement relative to the first and second wicks. A moving assembly is secured to the at least one blocking plate for moving the at least one blocking plate such that the at least one opening is moved into and out of alignment with the first and second wicks for adjusting escape of the evaporated fragrance from the first and second wicks.

The moving assembly includes a slide plate connected to the at least one blocking plate first for moving the at least one blocking plate to the different positions; and a slide member connected to the slide plate and which is manually actuable for moving the slide plate, and thereby the at least one blocking plate. The housing includes a slide opening and the slide member is accessible through the housing for manually moving the slide member.

The control circuit includes an actuation circuit for alternately controlling actuation of the first heater and the second heater. The actuation circuit alternately controls actuation of the first heater for a predetermined time interval and the second heater for the predetermined time interval. The actuation circuit further includes an override switch for controlling the actuation circuit to terminate actuation of the actuated heater and to actuate the non-actuated heater, regardless of the predetermined time interval, and then to start running of the predetermined time interval. Preferably, the actuation circuit includes a central processing unit.

A first light is visible through the housing and is activated when the first heater is actuated and a second light is visible through the housing and is activated when the second heater is actuated.

In a preferred embodiment, the first holder includes an inturned wall for receiving a neck of the first liquid fragrance container in a snap-fitting manner; and the second holder includes an inturned wall for receiving a neck of the second liquid fragrance container in a snap-fitting manner.

Specifically, each holder includes a cylindrical wall for receiving the neck in surrounding relation thereto, and the inturned wall is formed at a lower end of the cylindrical wall. In such case, each liquid fragrance container includes an outer lip on the neck for snap-fitting with the inturned wall of the respective holder.

There is also a heater housing for holding each heater, and the at least one blocking plate is movable between each heater housing and the respective wick.

In accordance with another aspect of the present invention, a multi-fragrance scent dispenser includes a housing having an outlet opening; a first heater; a second heater; a first holder in the housing for adjustably holding a first liquid fragrance container having a first wick extending out of the first liquid fragrance container at a desired height such that the first wick is surrounded by the first heater when the first liquid fragrance container is held by the first holder; a second holder in the housing for adjustably holding a first liquid fragrance, container having a second wick extending out of the second liquid fragrance container at a desired height such that the second wick is surrounded by the second heater when the second liquid fragrance container is held by the second holder; and a control circuit for selectively controlling activation of the first and second heaters.

Each holder includes an adjustable platform for supporting the respective liquid fragrance container at a plurality of different heights, a spring for biasing the respective platform in a direction toward the respective heater, and a limit for limiting movement of each platform in the direction.

Further, each holder includes a clamp for clamping a neck of the respective container. In this regard, there is a support for holding each heater at a respective position, and a connecting assembly for connecting the clamp to the support. Preferably, the connecting assembly includes a plurality of telescoping tubes which enables the clamp to move toward and away from the respective heater, with the telescoping tubes being held in desired positions relative to each other by friction.

Each clamp includes an adjustable clamping mechanism for clamping onto necks having different diameters. Specifically, the adjustable clamping mechanism includes a clamp housing; two scissor arms mounted in the clamp housing, each having an arcuate holding section, a spring assembly for normally biasing the scissor arms toward each other to clamp around the neck of a container, and extensions of the scissor arms for grasping in order to move the arcuate holder sections away from each other against the force of the spring assembly.

There is also a gel pack holder mounted immediately above each heater for holding a fragrance gel pack which emits a fragrance when heated by the respective heater. The gel pack holder includes a plurality of openings for emission of the vaporized gel fragrance to the outlet opening in the housing.

A fan can also be provided in the housing for blowing the vaporized fragrance to the outlet opening in the housing.

The housing preferably includes a base including the first heater, second heater, first holder, second holder, and control circuit; and a cover for covering the base and including the outlet opening.

Preferably, there are more than two bottles. Thus, there is at least one additional holder in the housing for adjustably holding at least one additional liquid fragrance container having a wick extending therefrom, desired height such that the respective wick thereof is surrounded by the at least one additional heater when the at least one liquid fragrance container is held by the at least one additional holder.

The above and other objects, features and advantages of the invention will become readily apparent from the following detailed description thereof which is to be read in connection with the accompanying drawings.

DETAILED DESCRIPTION

Figure 1:
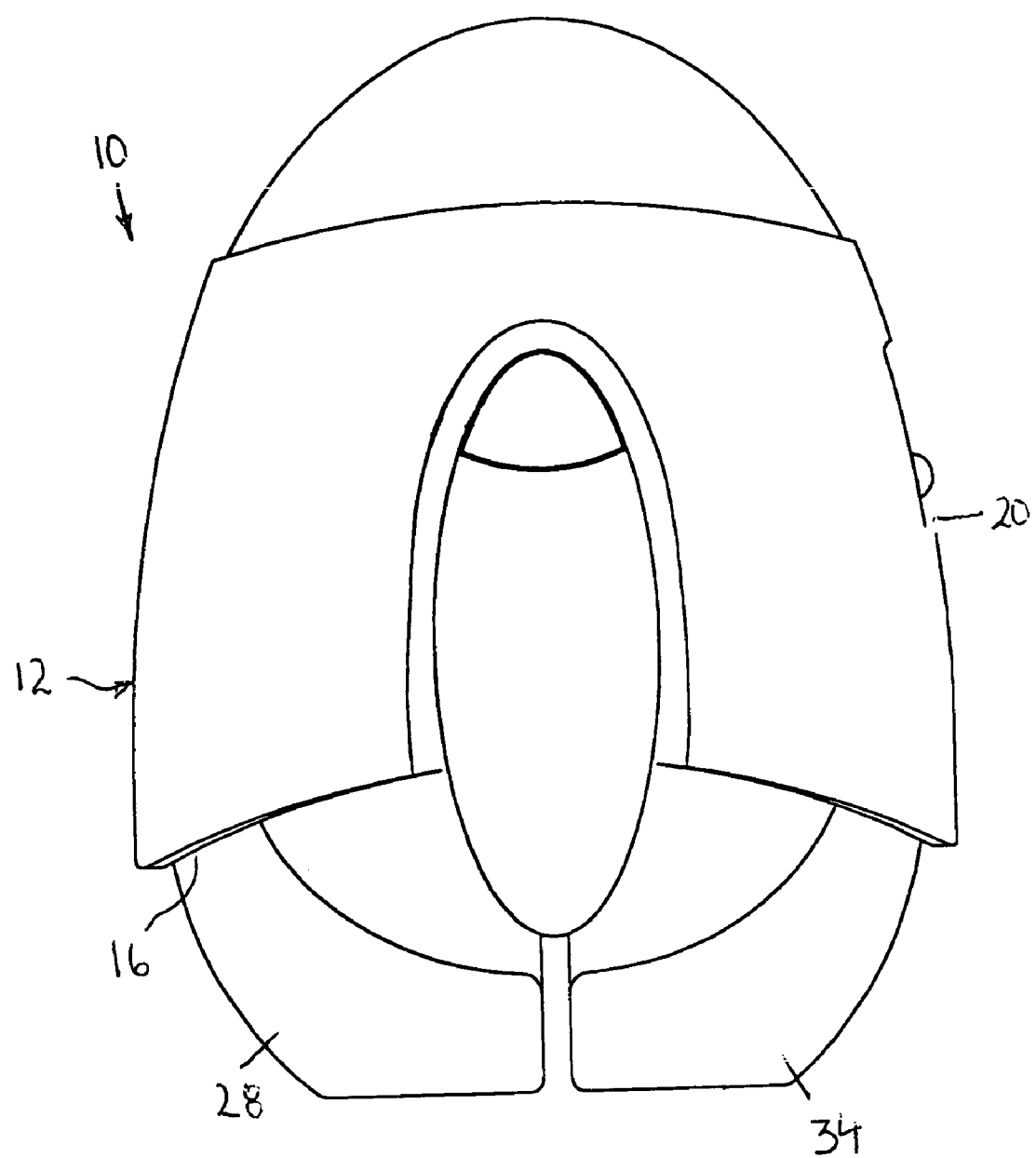
FIG. 1 is a front elevational view of a multi-fragrance scent dispenser according to the present invention.
Figure 2:
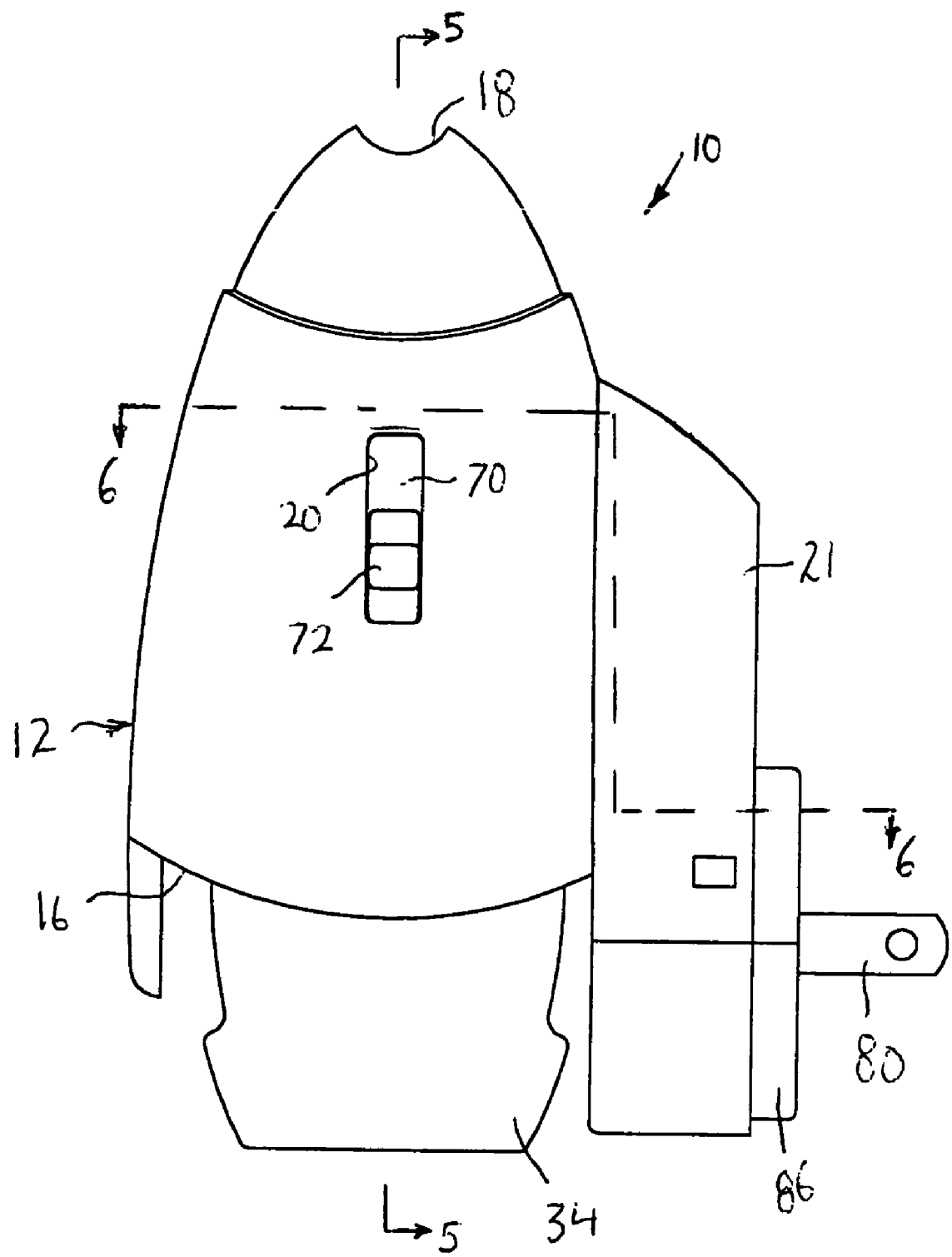
FIG. 2 is a side elevational view of the multi-fragrance scent dispenser.
Figure 3:
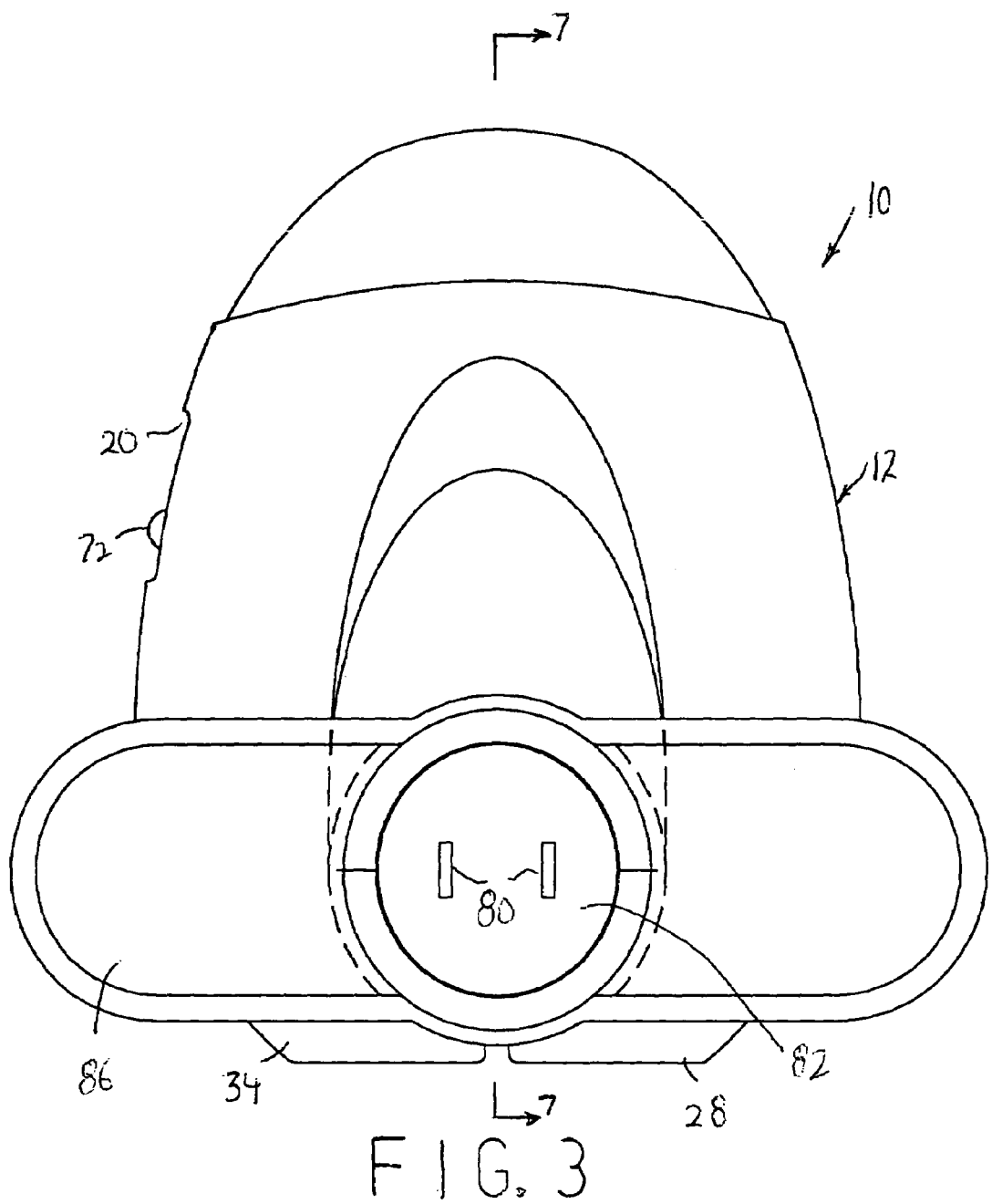
FIG. 3 is a rear elevational view of the multi-fragrance scent dispenser.
Figure 4:
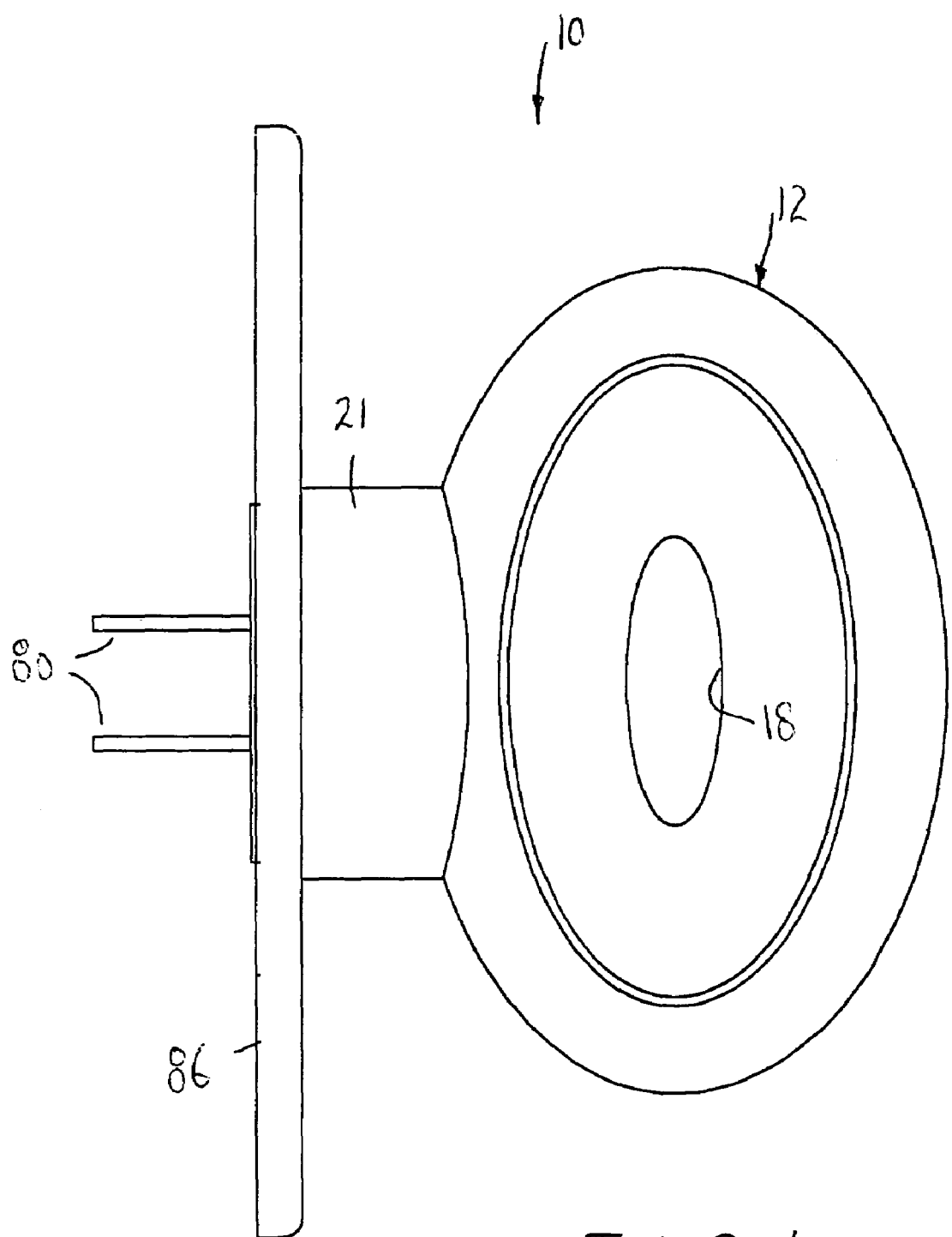
FIG. 4 is a top plan view of the multi-fragrance scent dispenser.
Figure 6:
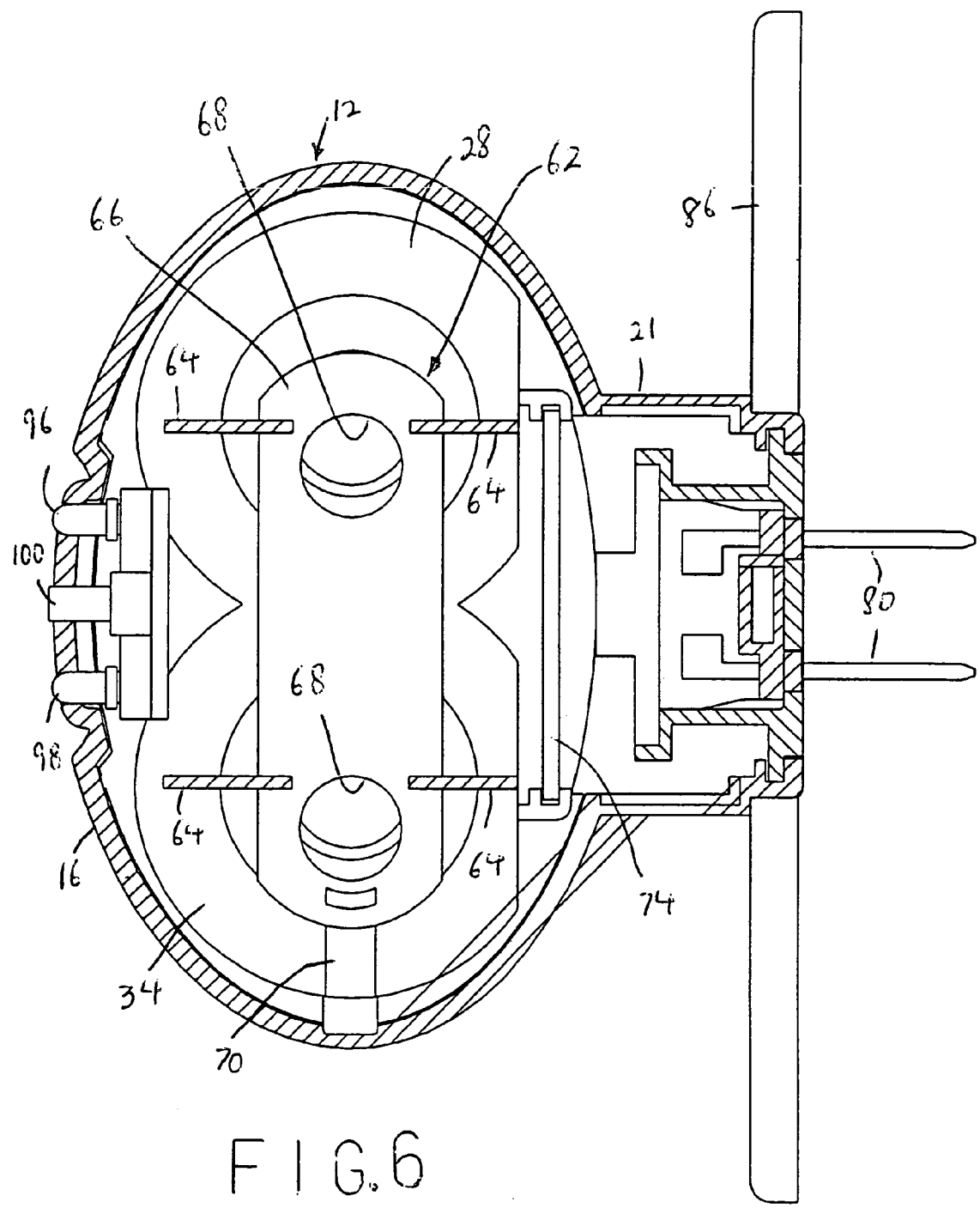
FIG. 6 is a cross-sectional view of the multi-fragrance scent dispenser of FIG. 3, taken along line 6—6 thereof.

Referring to the drawings in detail, a scent dispenser 10 according to the present invention includes a main housing 12 made of a suitable hard plastic material. Main housing 12 has a general shape of a rocket ship, although the present invention is not limited to this particular shape. Thus, main housing 12 tapers toward its upper end, and includes a peripheral wall 14 which has a lower open end 16 and a central opening 18 at the upper end thereof. There is also an elongated side opening 20 at the right side thereof in FIG. 1. As shown best in FIGS. 2, 6 and 7, main housing 12 includes a rear housing extension 21 which houses the electrical components, as will be described in more detail hereafter.

Figure 5:
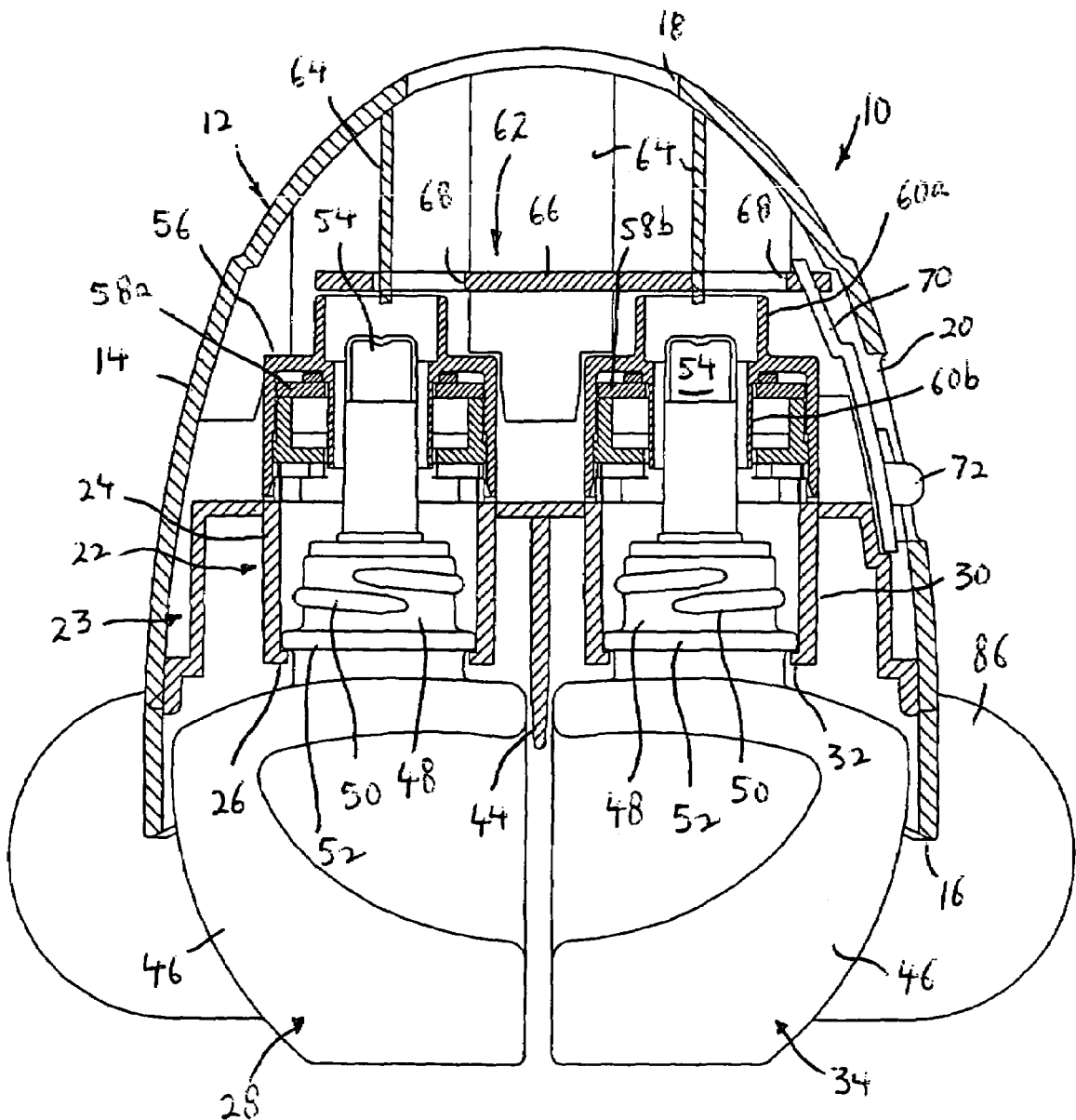
FIG. 5 is a cross-sectional view of the multi-fragrance scent dispenser of FIG. 2, taken along line 5—5 thereof.
Figure 7:
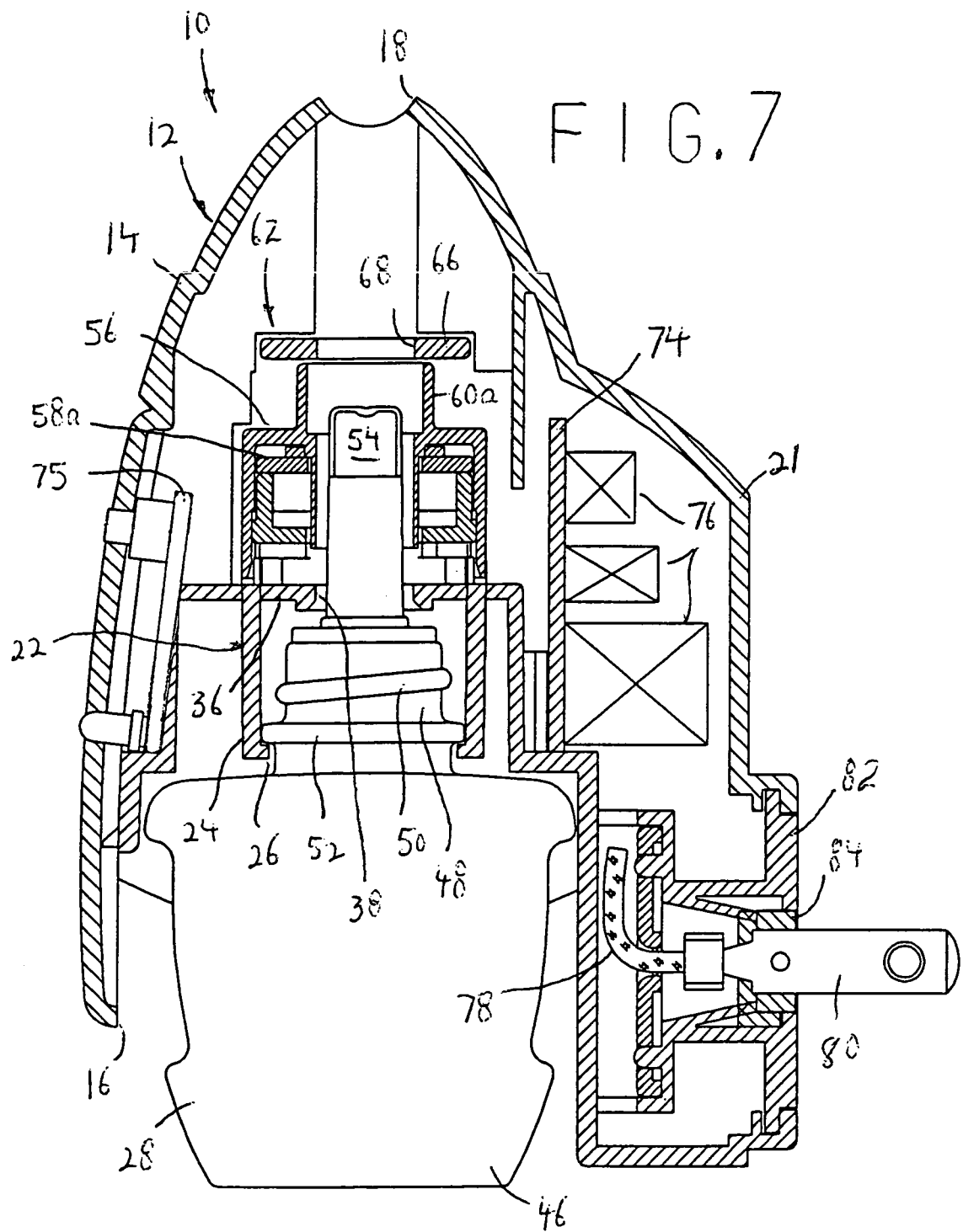
FIG. 7 is a cross-sectional view of the multi-fragrance scent dispenser of FIG. 3, taken along line 7—7 thereof.

As shown best in FIGS. 5 and 7, a fragrance bottle support 22 is positioned within housing 12 and is secured by an annular securing wall 23 to the inner surface of peripheral wall 14. Fragrance bottle support 22 includes a first cylindrical wall 24 having a lower inturned annular lip 26 for holding a first bottle 28 containing a liquid fragrance and a second cylindrical wall 30 having a lower inturned annular lip 32 for holding a second bottle 34 containing a second, different liquid fragrance. An upper wall 36 partially closes the upper end of each cylindrical wall 24 and 30, and each upper wall 36 has an opening 38 therein. A divider wall 44 separates first cylindrical wall 24 from second cylindrical wall 30.

Bottles 28 and 34 each have a main body 46 and a neck portion 48 with threads 50 thereon for threadedly receiving a cap (not shown) thereon. An annular ledge 52 is formed on neck portion 48 immediately below threads 50 and has dimensions similar to the inner dimensions of first cylindrical walls 24 and 30. When bottle 28 is inserted through lower open end 16, neck portion 48 thereof is inserted through the lower open end of first cylindrical wall 24. Continued insertion of bottle 28 results in annular ledge 52 being forced through lower inturned annular lip 26, whereupon annular ledge 52 is then captured by lower inturned annular lip 26. A similar operation occurs with respect to bottle 34, second cylindrical wall 30 and lower inturned annular lip 32, whereupon annular ledge 52 of second bottle 34 is captured by lower inturned annular lip 32.

The present invention is not limited to these bottle shapes, and any other suitable bottle shapes can be used, such as shown by bottles 28a–28g in FIGS. 15a–15g.

A wick 54 extends outwardly from the open end of each neck portion 48 and through the respective opening 38. Each wick 54 carries liquid from the respective bottle 28 or 34 to the upper end of the wick 54.

Heater housings 56 surround each wick 54 and encase heater assemblies 58a and 58b, respectively. When the respective heater assembly 58a or 58b is activated, the heat therefrom is transferred through the heater housing 56 to the respective wick 54. As a result, the liquid at the upper end of the wick 54 is vaporized by the heat, and released to atmosphere through opening 18.

Each heater housing 56 includes an inner annular wall 60 surrounding the respective wick 54. Inner annular wall 60 includes an upper annular wall section 60a of a first inner diameter and a lower annular wall section 60b of a second inner diameter which is less than the first inner diameter and which is connected to upper annular wall section 60a by an annular shoulder 60c.

In accordance with an aspect of the present invention, a fragrance blocking assembly 62 is provided for blocking some of the evaporation of the fragrance by heater assemblies 58a and 58b. Specifically, fragrance blocking assembly 62 includes a blocking plate 66 having openings 68 which can be in alignment with the inner diameters of upper annular wall sections 60a in order to permit the escape of vaporized fragrances. As will be explained hereafter, blocking plate 66 can move horizontally above heater assemblies 58a and 58b.

Figure 10:
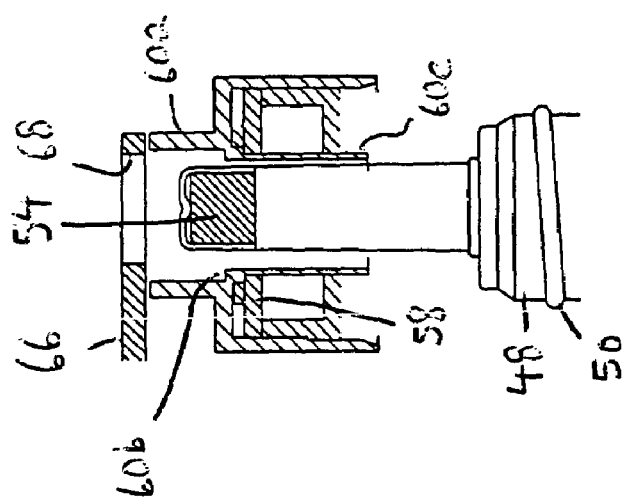
FIG. 10 is an enlarged cross-sectional view of the heater, wick and blocking plate of the multi-fragrance scent dispenser of FIG. 1, in the highest position of the blocking plate.
Figure 9:
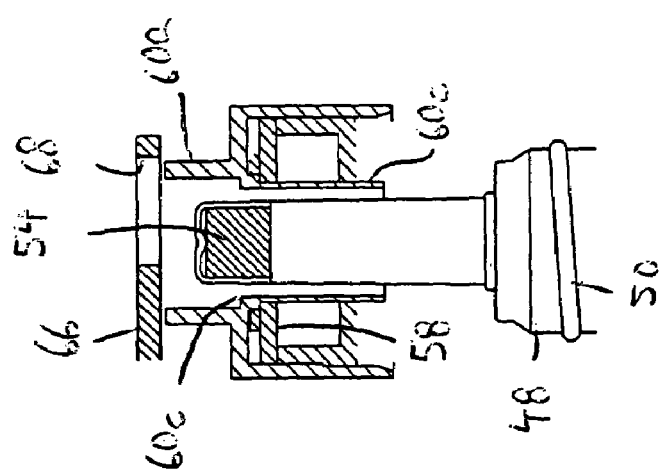
FIG. 9 is an enlarged cross-sectional view of the heater, wick and blocking plate of the multi-fragrance scent dispenser of FIG. 1, in a middle position of the blocking plate.
Figure 8:
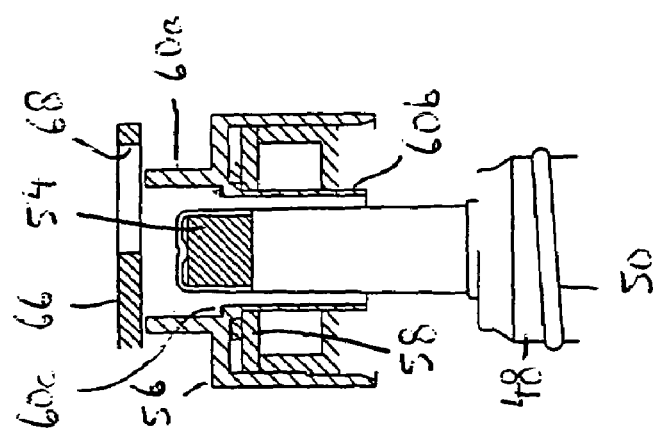
FIG. 8 is an enlarged cross-sectional view of the heater, wick and blocking plate of the multi-fragrance scent dispenser of FIG. 1, in the lowest position of the blocking plate.
Figure 11:
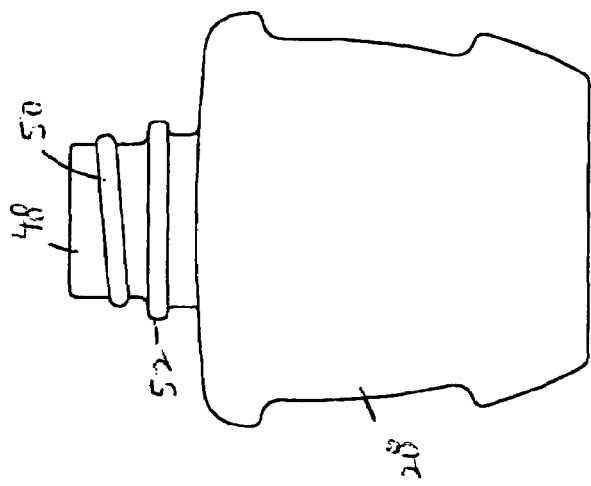
FIG. 11 is a side elevational view of a bottle of fragrance that can be used with the present invention.
Figure 12:
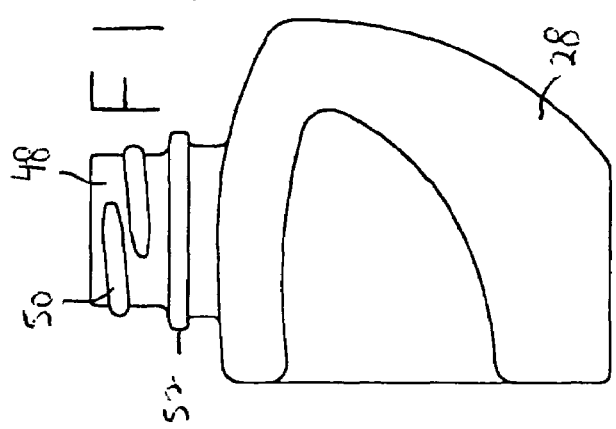
FIG. 12 is a front elevational view of the bottle of FIG. 11.
Figure 13:
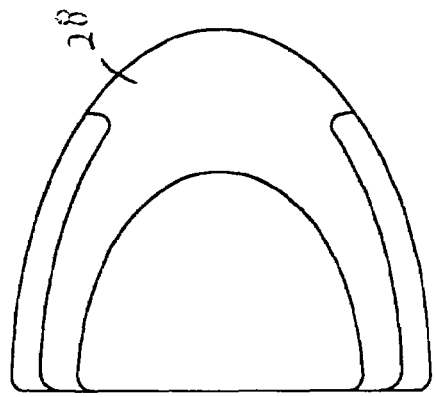
FIG. 13 is a bottom plan view of the bottle of FIG. 11.

Thus, as shown in FIG. 8, when blocking plate 66 is in a first position, openings 68 are out of alignment with the openings provided by upper annular wall sections 60a, thereby blocking some of the evaporated fragrance. FIG. 9 shows an intermediate position where openings 68 are out of alignment with the openings provided by upper annular wall sections 60a to a lesser extent, thereby blocking a lesser amount of the evaporated fragrance. Finally, as shown in FIG. 10, openings 68 are in alignment with the openings provided by upper annular wall sections 60a, thereby permitting escape of all of the evaporated fragrance. As a result, a simple fragrance adjusting mechanism is provided.

Although only three positions are shown, it will be appreciated that the positions of blocking plate 66 can be infinitely variable, and is not limited to these three positions, which are shown only for explanatory purposes.

In order to move blocking plate 66 toward and away from heater assemblies 58a and 58b, blocking plate 66 is mounted within guides 64 that extend above, to the sides and to the bottom of blocking plate 66 so that only horizontal linear movement of blocking plate 66 is permitted between the positions shown in FIGS. 8–10.

A slide plate 70 is connected to one end of blocking plate 66, and a button 72 is mounted to slide plate 70 and extends out through side opening 20 for movement therealong.

Thus, as button 72 is moved along side opening 20, upper plate 66 is moved up and down therewith, thereby adjusting the positions of blocking plates 64, and thereby adjusting the heat that is imparted to wicks 54. As a result, the amount of evaporated fragrance that escapes is adjusted, so that the amount of scent that is provided is also adjusted.

Button 72 and/or slide plate 70 are maintained in position by friction ribs on the housing.

A printed circuit board 74 is provided in rear housing extension 21 and includes various circuit components 76 thereon, and a printed circuit board 75 is mounted at the front of main housing 12.

Printed circuit board 74 is connected through a wire 78 with two plug blades 80 which extend out from rear housing extension 21 for insertion into a conventional wall socket for the supply of electricity, for example, 125 volt AC input. Printed circuit board 74 is electrically connected with heater assemblies 58a and 58b for controlling operation thereof.

Plug blades 80 can rotated in a turning plug 82 of a plug blade bracket 84, in order to adjust the angle and orientation of scent dispenser 10. A horizontal elongated socket blocking plate 86 is preferably secured to rear housing extension 21 to block the socket when plug blades 80 are plugged into the socket.

As an alternative, wire 78 can extend out of rear housing extension 21 and be connected to an electrical plug having plug blades 80. In this manner, scent dispenser 10 can be mounted on a flat surface, such as a table.

Figure 14:
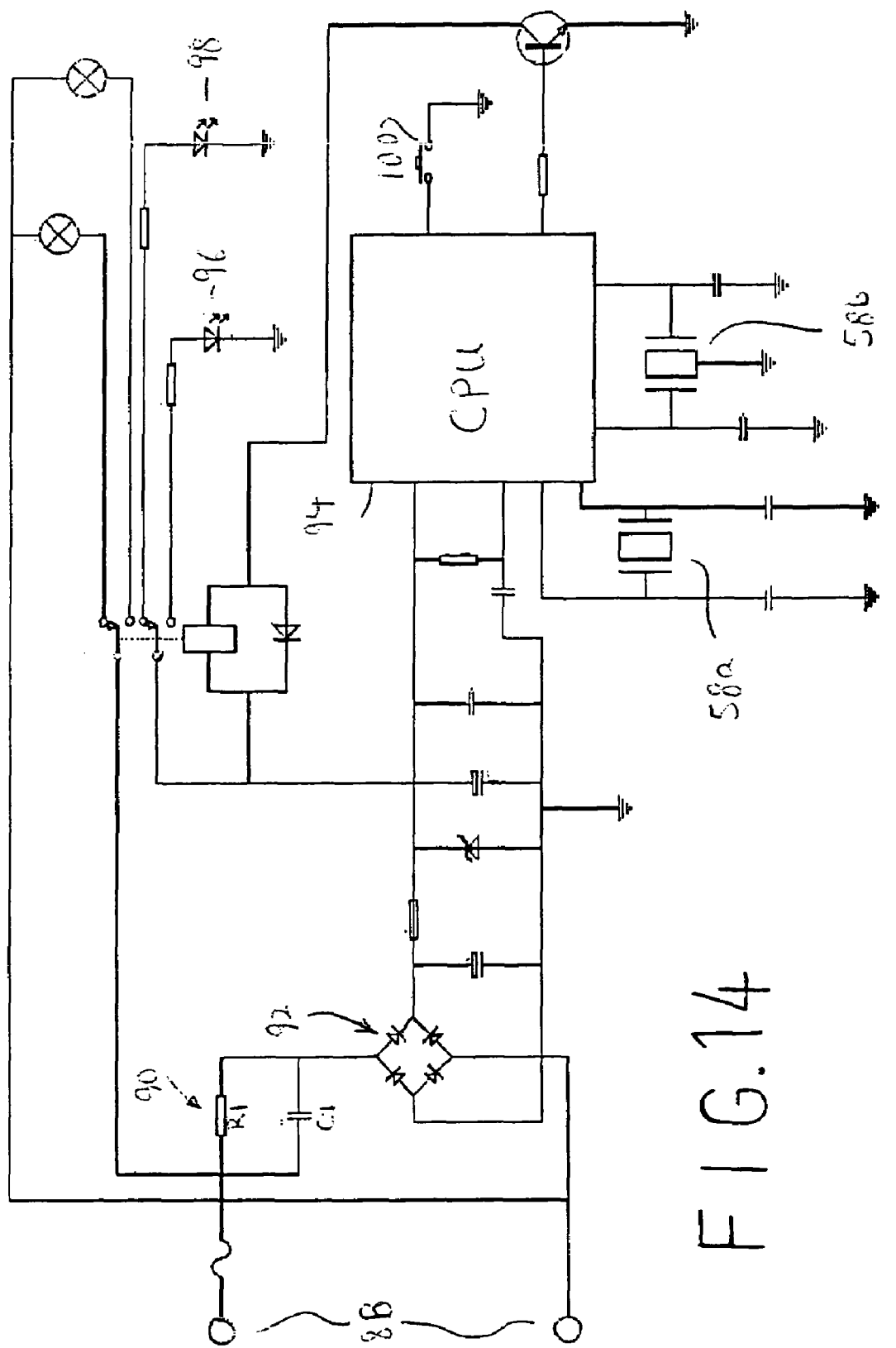
FIG. 14 is a circuit wiring diagram of the main circuit board of the multi-fragrance scent dispenser.
Figure 15:
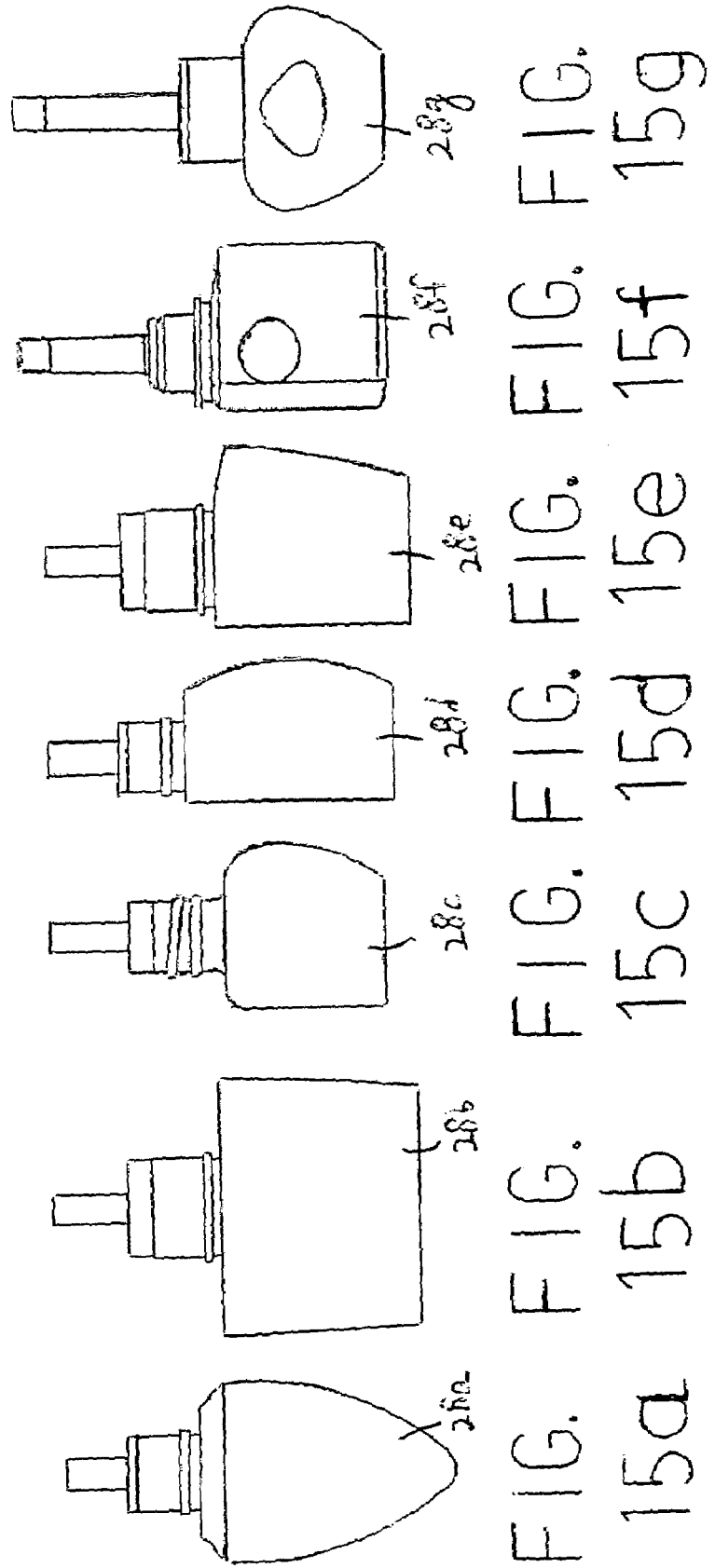
FIGS. 15a–15g are elevational views of alternative shaped bottles of fragrances that can be used with the present invention.
Figure 16:
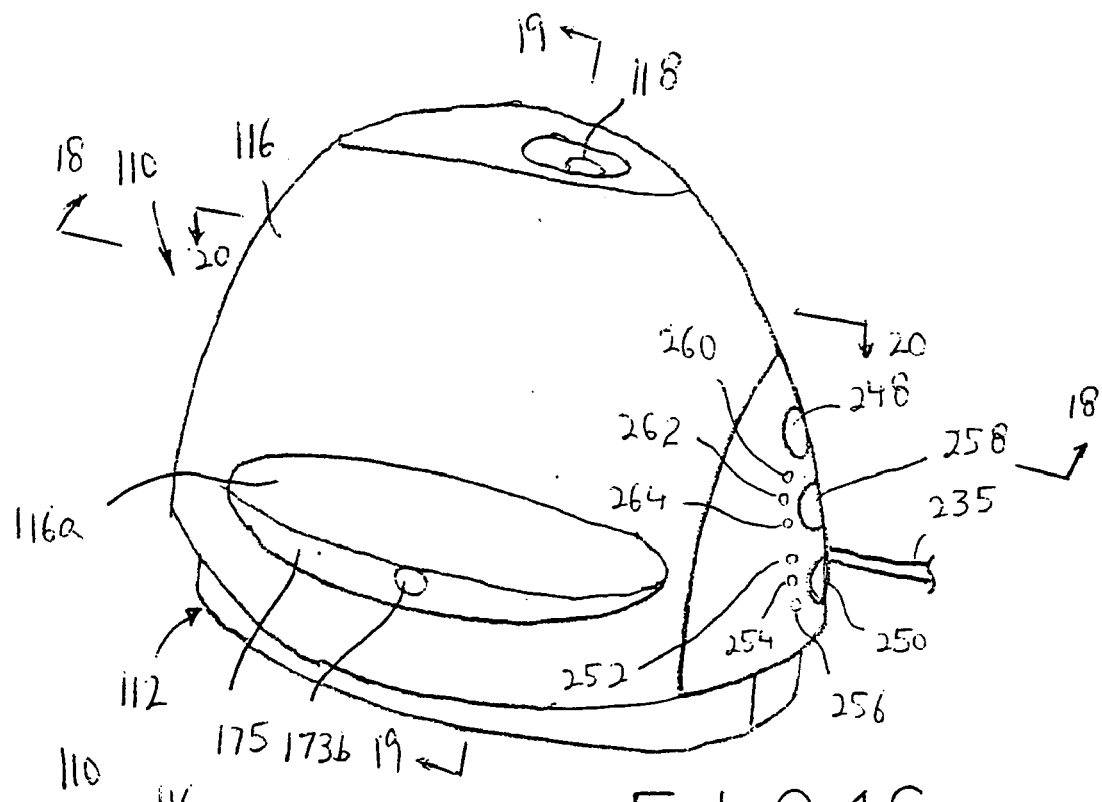
FIG. 16 is a perspective view of a scent dispenser according to another embodiment of the present invention, with the cover positioned thereon.

The circuitry of circuit components 76 and their connections on printed circuit boards 74 and 75 will now be discussed in detail with reference to FIG. 14. As shown therein, plug blades 80 are connected to electrical connections 88 of an AC input, for example, at 125 VAC, which is supplied through a voltage stepdown capacitor/resistor circuit 90 comprised of a resistor R1 and capacitor C1 to a rectifier circuit 92 in order to provide a DC input. The DC input is then supplied to a central processing unit (CPU) 94 to supply power therefor, with central unit selectively supplying power to heater assemblies 58a and 58b.

Once scent dispenser 10 is plugged into an electrical socket, power is supplied to CPU 94 to start operation. CPU 94 is controlled by internal software to first activate heater assembly 58a for a predetermined period of time, for example, twelve hours. At the end of the twelve hour time period, CPU 94 automatically terminates power to heater assembly 58a and then activates heater assembly 58b for the same twelve hour period. During this latter activation, a new fragrance bottle 28 can be inserted therein in order to replenish the liquid fragrance for the next twelve hour cycle, and so on. In this manner, a person does not become accustomed to a particular scent. Whenever heater assembly 58a is activated, a light emitting diode (LED) 96 on printed circuit board 75 and which is visible through an opening in the left side of the front of main housing 12, is activated to light up. On the other hand, whenever heater assembly 58b is activated, a light emitting diode (LED) 98 on printed circuit board 75 and which is visible through an opening in the right side of the front of main housing 12, is activated to light up.

A person can override the twelve hour programming. In this regard, a tactile switch 100 which is accessible through an opening the front of main housing 12, connects an input of CPU 94 to ground to control CPU to automatically switch over and activate the other heater assembly 58a or 58b and activate the other fragrance for the start of a new twelve hour time period, and thereby start the cycles running again.

Referring now to FIGS. 16–29, a scent dispenser 110 according to another embodiment of the present invention will now be described in detail.

Scent dispenser 110 according to the present invention includes a main housing 112 made of a suitable hard plastic material. Main housing 112 includes a base 114 for housing the fragrance materials, the heater assemblies and the circuitry, and a dome cover 116 for covering base 114. Cover 116 includes an opening 118 at the upper end thereof for emission of the vaporized scents.

Base 114 includes a generally lower oval shaped section 120 with a central generally oval shaped recess 122. Vertically extending end walls 124 and 126 are provided at opposite ends of the oval shaped recess 122, and vertically extending divider walls 128 and 130 divide the area between end walls 124 and 126 into three bottle holding areas 132. It will be appreciated, however, that the present invention is not limited to three bottle holding areas 132 and can be provided with more or less than three such areas. End walls 124 and 126 having inwardly extending stops 134 at the same height, and divider walls 128 and 130 have stops 136 extending from opposite sides at the upper ends thereof. Bottle holding areas 132 are further defined by a rear wall 138 having stops 140 and a front wall 142 having stops 144.

Figure 17:
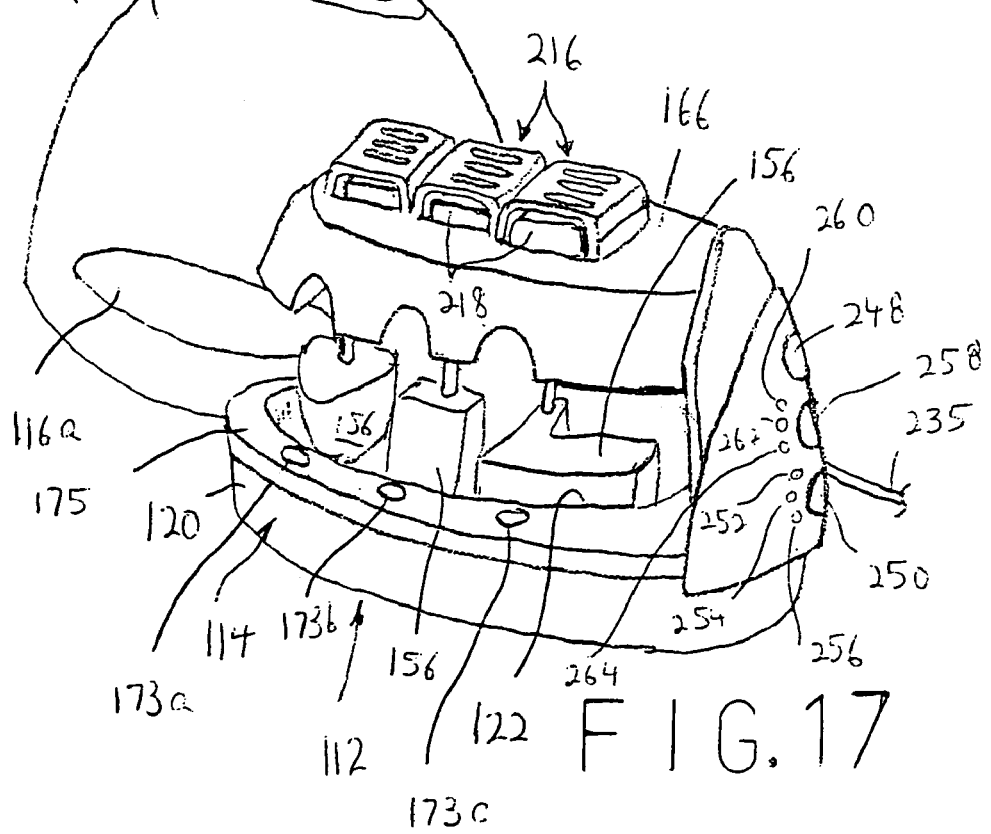
FIG. 17 is a perspective view of the scent dispenser of FIG. 16, with the cover removed.

The respective walls defining bottle holding areas 132 are not shown in FIG. 17 for the sake of clarity in the drawing.

Figure 20:
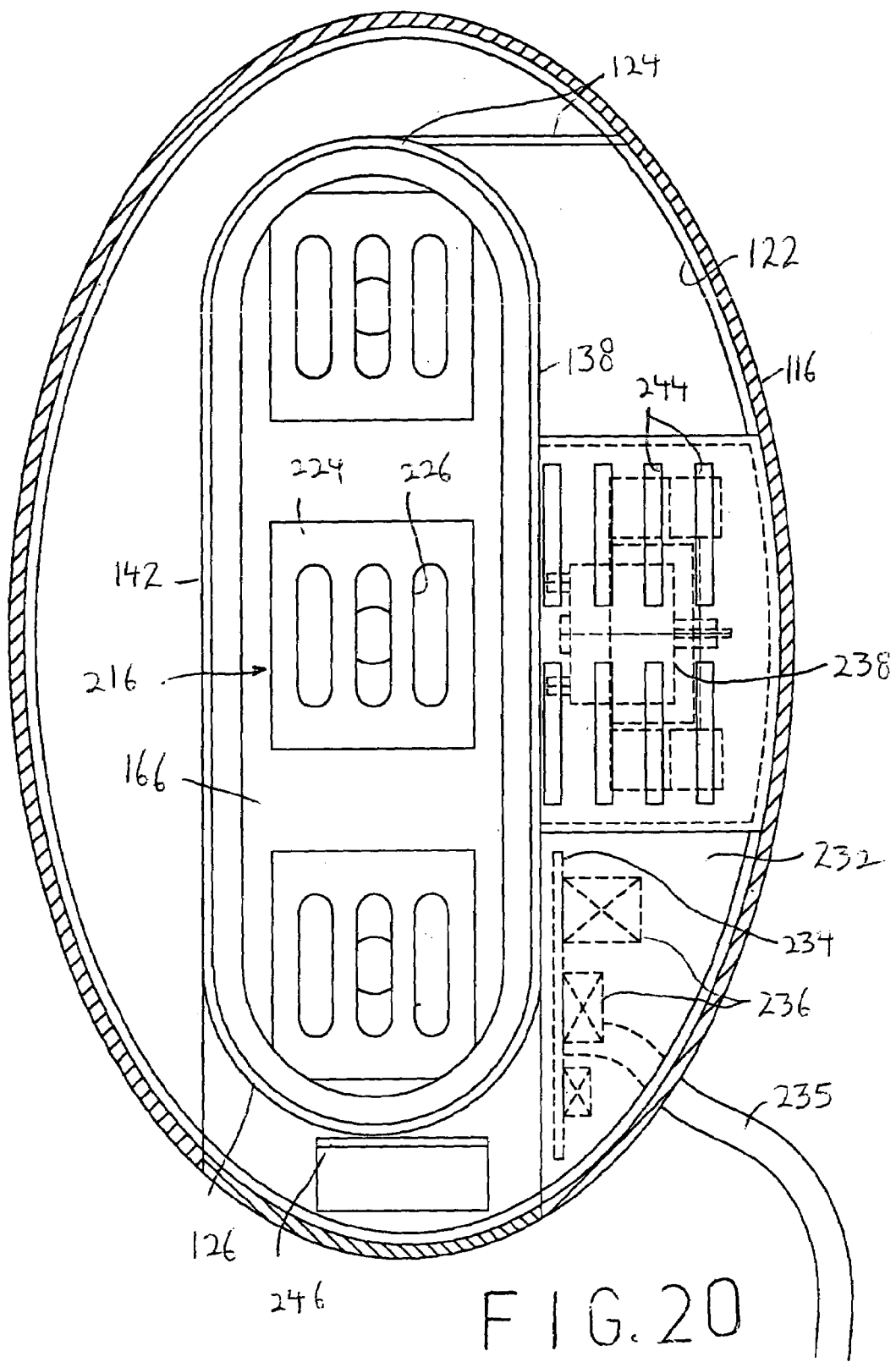
FIG. 20 is a cross-sectional view of the scent dispenser of FIG. 16, taken along line 20—20 thereof.
Figure 21:
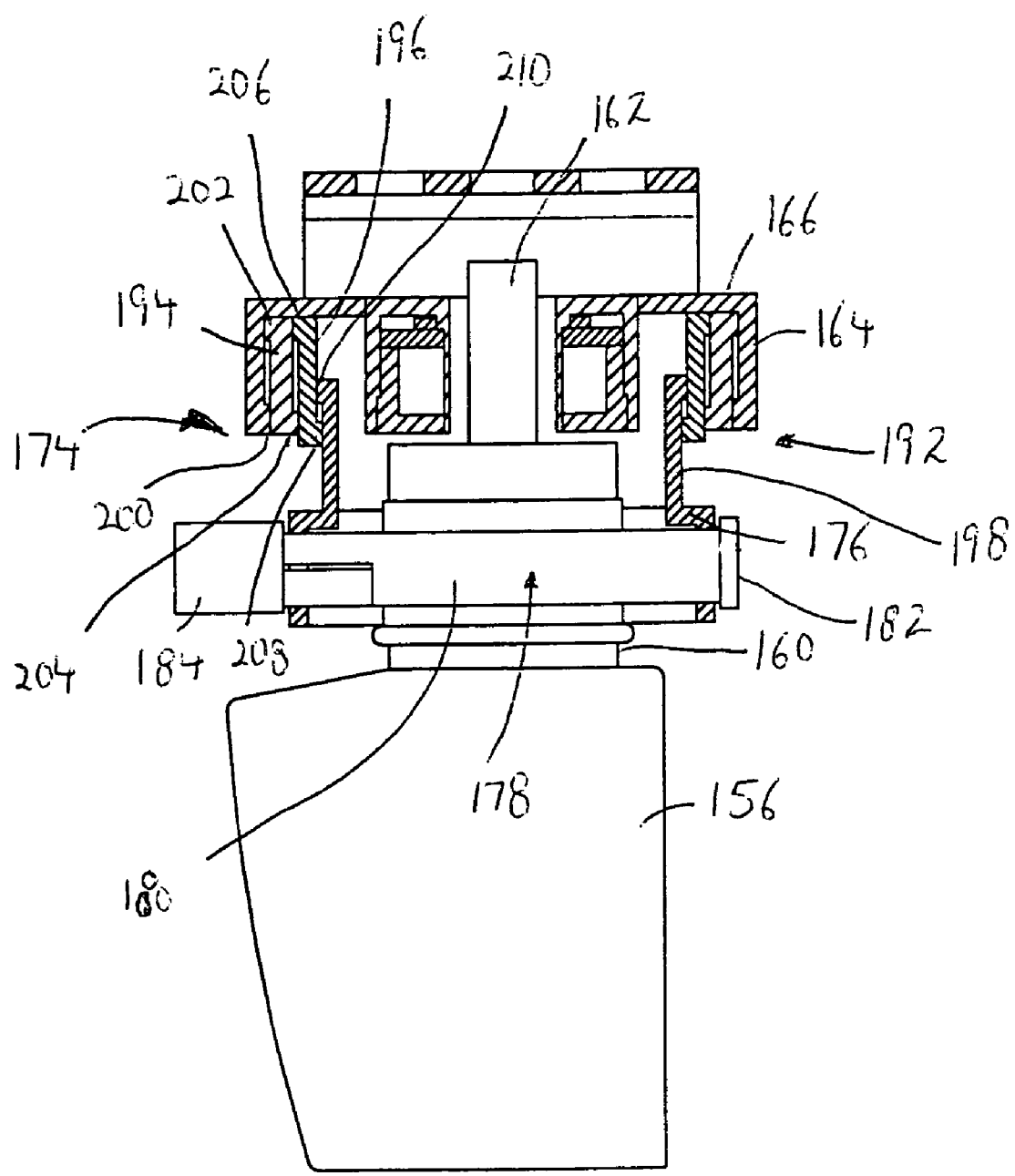
FIG. 21 is an enlarged cross-sectional view of the clamp mechanism, adjustment arrangement, and gel pack housing.

Preferably, walls 124, 126, 138 and 142 are arranged in an oval configuration, as shown in FIG. 20.

A platform 146 is slidably positioned in each bottle holding area 132 and is biased upwardly therein by a coil spring 148. In this regard, a circular boss 150 extends centrally from the lower end of each platform 146 in surrounding relation to an opening 152 in each platform 146.

One end of the respective coil spring 148 extends around each circular boss 150. A circular boss 154 extends from the bottom wall 114a of base 114 in each bottle holding area 132 for receiving the opposite end of the respective coil spring 148. Stops 134, 136, 140 and 144 function as limits as to the upward movement of platforms 146.

A fragrance bottle 156 sits on the upper surface of each platform 146 and each fragrance bottle 156 includes a main body 158 and a neck portion 160. The neck portions 160 are not shown in FIG. 17 for the sake of clarity in the drawing. A wick 162 extends outwardly from the upper open end of each bottle 156, either from main body 158 or from neck portion 160. Each wick 162 carries liquid from the respective bottle 156 to the upper end of the wick 162. The length of each wick 162 will depend on the height of the bottle 156 and the weight of the bottle 156, that is, the extent that the respective platform 146 compresses the associated coil spring 148.

A cylindrical support wall 164 extends above each bottle 156 and is mounted to end walls 124 and 126 and to rear wall 138 by an upper plate 166 having openings 168 centrally located relative to each cylindrical support wall 164. Cylindrical heater housings 170 extend within openings 168 and extend downwardly from upper plate 166 in surrounding relation to each wick 162 and in surrounding relation to each respective opening 168. Each heater housing 170 has a central opening 171 through which the wick 162 extends. Each heater housing 170 houses a heater assembly 172 therein. When the respective heater assembly 172 is activated, the heat therefrom is transferred through the heater housing 170 to the respective wick 162. As a result, the liquid at the upper end of the wick 162 is vaporized by the heat, and released to atmosphere through opening 118. Further, lights 173a–173c are provided on a ledge 175 of base 114 in front of each bottle 156. Thus, the respective light 173a–173c is illuminated in correspondence with the heater assembly 172 then being activated. The illuminated light 173a, 173b or 173c can be viewed through a window 116a in cover 116.

In order to stably support bottles 156 at different heights, due to different shapes, configurations and weights of bottles 156, a clamping mechanism 174 extends down from each cylindrical support wall 164. Specifically, each clamping mechanism 174 includes a hollow, rectangular clamp housing 176. Two scissor-like arms 178 are horizontally positioned in each housing 176. Each scissor-like arm 178 has an arcuate center section 180, with the two arcuate center sections 180 being in opposing relation to each other, for engaging around the neck 160 of a bottle 156. Each scissor-like arm 178 includes a rear extension 182 extending rearwardly of arcuate center section 180 through a slot 183 in a rear wall 176a of housing 176, and a front extension 184 extending forwardly of arcuate center section 180 through a slot 186 in a front wall 176b of housing 176.

Figure 18:
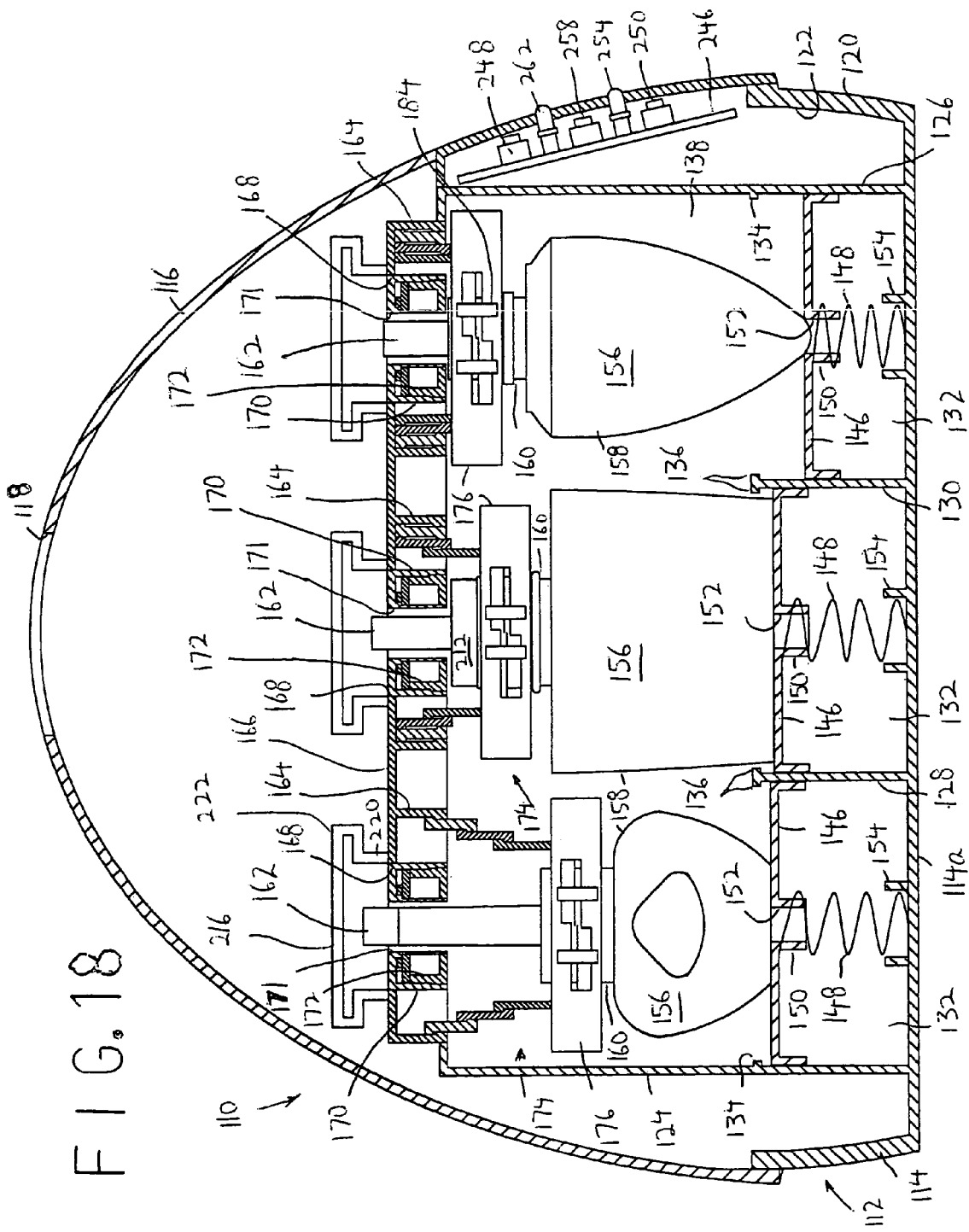
FIG. 18 is a cross-sectional view of the scent dispenser of FIG. 16, taken along line 18—18 thereof.

Side walls 176c and 176d of each housing 176 include opposing cylindrical bosses 188, and coil springs 190 extend between posts 191 on the outer surfaces of arcuate center sections 180 and the inner surfaces of side walls 176c and 176d around bosses 188. An opening 177 is provided in the upper wall 176e of housing 176, and an opening 179 is provided in the lower wall 176f of housing 176 for receiving a neck 160 and wick 162 therethrough. Telescoping tube members 212 and 214 can also be provided in surrounding relation to upper opening 177 for further adjustment, as shown in FIGS. 18 and 23.

Figure 22:
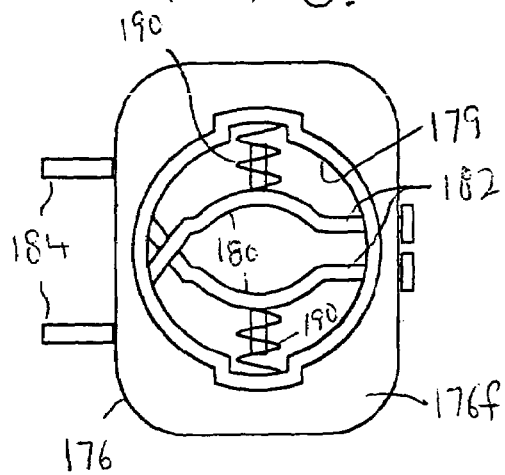
FIG. 22 is a bottom plan view of the clamping mechanism.
Figure 23:
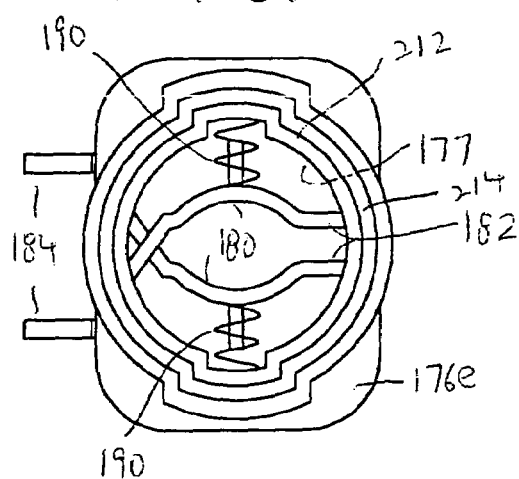
FIG. 23 is a top plan view of the clamping mechanism.
Figure 24:
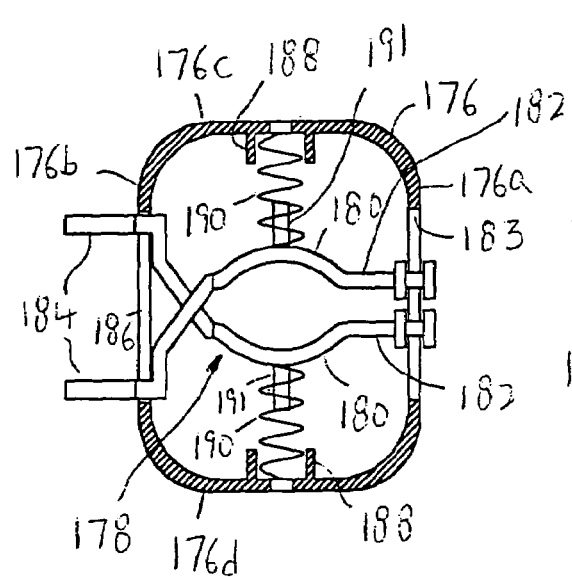
FIG. 24 is a cross-sectional view of the clamping mechanism shown in the clamping position.

Thus, as shown in FIGS. 22–24, coil springs 190 normally bias arcuate center sections 180 toward each other.

Figure 25:
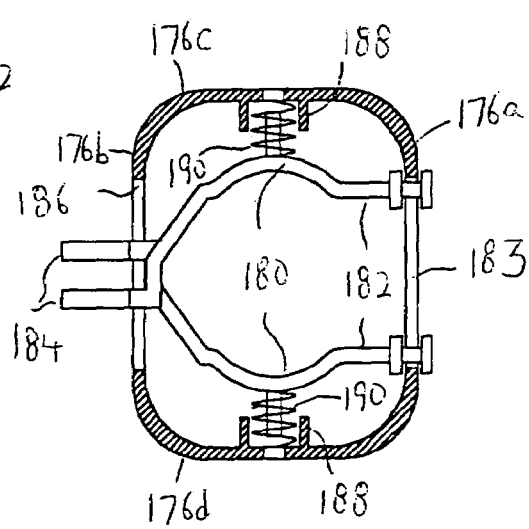
FIG. 25 is a cross-sectional view of the clamping mechanism shown in the release position.
Figure 26:
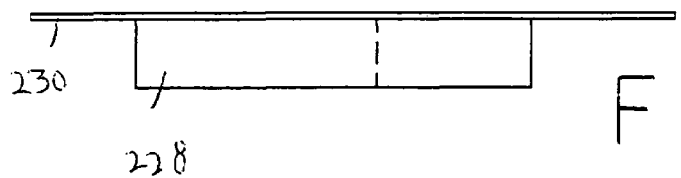
FIG. 26 is a side elevational view of a gel pack.
Figure 27:
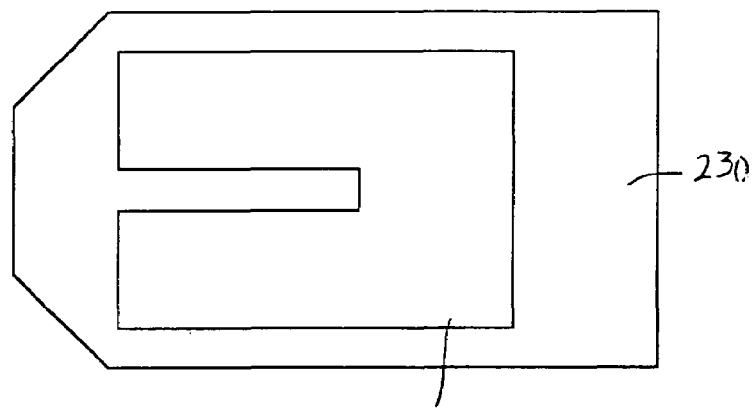
FIG. 27 is a bottom plan view of the gel pack.
Figure 28:
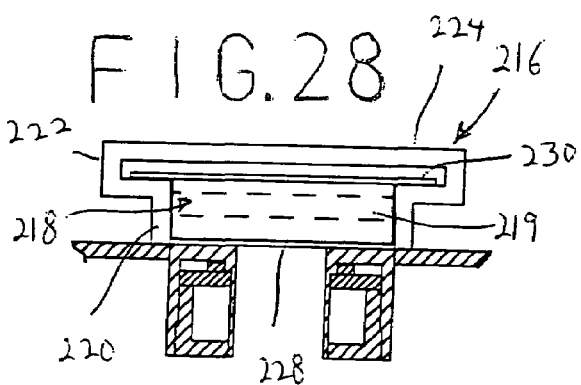
FIG. 28 is a cross-sectional view of a heater assembly and gel pack housing holding a gel pack.
Figure 29:
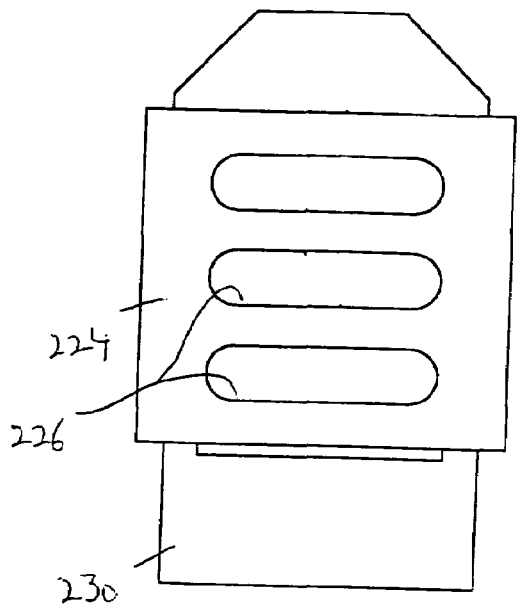
FIG. 29 is a top plan view of the gel pack housing holding a gel pack.

However, when front extensions 184 are squeezed together toward each other, as shown in FIG. 25, arcuate center sections 180 move away from each other to permit entry of the neck 160 of a bottle 156, whereupon front extensions 184 are released. As a result, coil springs 190 bias arcuate center sections 180 in a grasping relation around the neck 160 of bottle 156. Because the outer diameters of neck portions 160 of bottles 156 vary in size, for example, from diameters in the range of about 14 mm to 24 mm, arcuate center sections 180 can be arranged to clamp any size bottle 156.

Each clamping mechanism 174 further includes an adjustment arrangement 192 for vertically moving hollow, rectangular clamp housing 176 in order to adjust for different height bottle 156. Adjustment arrangement 192 includes three telescopically arranged tubes 194, 196 and 198 telescopically received in cylindrical support wall 164 and which stay in a set position by means of friction between the tubes 194, 196 and 198, and such that the tubes will also not rotate relative to each other. Specifically, a radially inwardly extending annular lip 200 is formed at the lower end of each cylindrical support wall 164. Tube 194 slidably fits within cylindrical support wall 164 and has a radially outwardly extending annular lip 202 at the upper end thereof with outer dimensions similar to the inner dimensions of cylindrical support wall 164. Thus, annular lip 200 engages with annular lip 202 to prevent escape of tube 194 from cylindrical support wall 164, while permitting sliding movement therein.

A radially inwardly extending annular lip 204 is formed at the lower end of tube 194. Tube 196 slidably fits within tube 194 and has a radially outwardly extending annular lip 206 at the upper end thereof with outer dimensions similar to the inner dimensions of tube 194. Thus, annular lip 204 engages with annular lip 206 to prevent escape of tube 196 from tube 194, while permitting sliding movement therein.

A radially inwardly extending annular lip 208 is formed at the lower end of tube 196. Tube 198 slidably fits within tube 196 and has a radially outwardly extending annular lip 210 at the upper end thereof with outer dimensions similar to the inner dimensions of tube 196. Thus, annular lip 208 engages with annular lip 210 to prevent escape of tube 198 from tube 196, while permitting sliding movement therein. The lower end of tube 198 is fixed to clamp housing 176.

Alternatively, or in addition to fragrance bottles 156, a gel pack housing 216 is mounted on the upper surface of upper plate 166 for holding a fragrance gel pack 218 above each heater assembly 172. Specifically, each gel pack housing 216 includes a lower rectangular section 220 that is open at the lower end, and the front and rear thereof. An upper rectangular section 222 of a larger width is mounted to the upper end of lower rectangular section 220 and is open at the lower end thereof so as to be in open communication with lower rectangular section 220. Upper rectangular section 222 is also open at the front and rear thereof. The upper wall 224 of upper rectangular section 222 includes elongated openings 226 through which the scent can escape to opening 118 in cover 116. In this manner, each gel pack 218 includes a rectangular container 228 of a material that does not permit escape of the gel 219 in liquid form, but permits escape of the gaseous fragrance when the gel vaporizes. A wider porous and rigid holder 230 is secured to the upper surface of container 228. Thus, when holder 230 slides within upper rectangular section 222, container 228 is slid within lower rectangular section 220 immediately above opening 171 so that the gel 219 can be vaporized and escape to the atmosphere to emit the fragrance.

Rear wall 138, along with a rear wall 112a of main housing 112, end wall 124, and a top wall 231, function to define a circuit area 232 for holding a printed circuit board 234 having circuit components 236 thereon that control operation of scent dispenser 110, in the same manner as printed circuit board 74 and circuit components 76. Printed circuit board 234 is connected through wires 235 with two plug blades (not shown) which extend out from housing 112 for insertion into a conventional wall socket for the supply of electricity, for example, 125 volt AC input. Printed circuit board 234 is electrically connected with heater assemblies 172 for controlling operation thereof.

Figure 19:
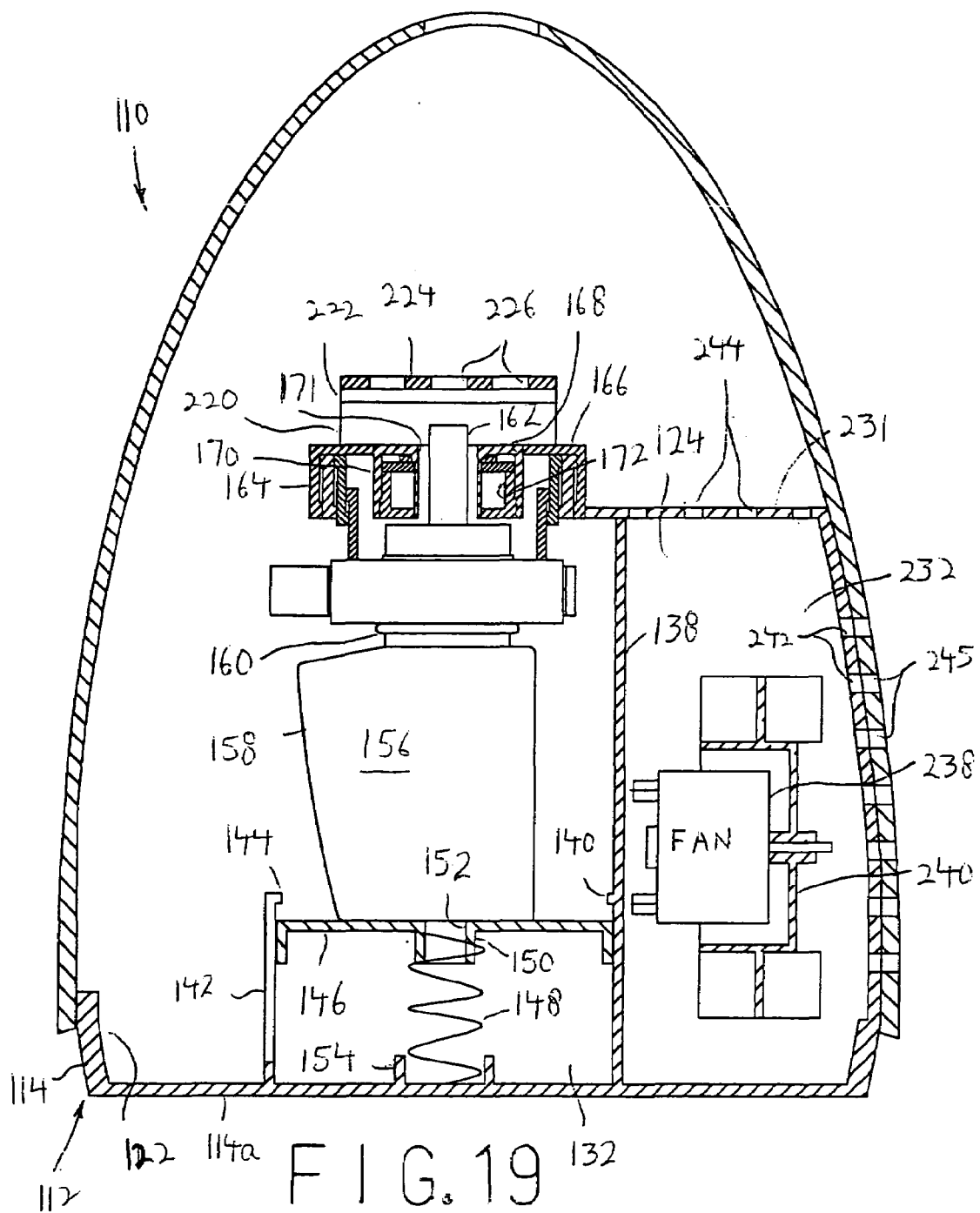
FIG. 19 is a cross-sectional view of the scent dispenser of FIG. 16, taken along line 19—19 thereof.

In addition, a fan 238 is mounted to a fan support 240 in circuit area 232. In this regard, rear wall 112a and top wall 231 are provided with openings 242 and 244, respectively, for ventilation. Cover 116 also includes openings 245 in the rear wall thereof which are in alignment with openings 242 when cover 116 is assembled with base 114, as shown in FIG. 19. Thus, fan 238 pulls air from the outside of housing 112 through openings 242 and blows the air out through openings 244. As a result, the vaporized fragrance is entrained by the air from openings 244 and carried out through opening 118 in cover 116. Fan 238 is controlled by the central processing unit (CPU) of circuit components 236.

A printed circuit board 246 is mounted inside of main housing 112 and at one side thereof, and is electrically connected to main printed circuit board 234. Printed circuit board 246 includes various control buttons and light indicators which are accessible through side openings in housing 112. Specifically, there is a toggle switch 248 that turns the scent dispenser 110 on and off, and functions as a main switch. In addition, there is a heat adjustment switch 250 that can control the energy supplied to heater assemblies 172 to control the heat to be low, medium or high. Each depression of button switch 250 toggles the setting between low, medium and high. In addition, there are three light emitting diodes (LEDs) 252, 254 and 256 to indicate the heat setting of low, medium and high. A third button switch 258 is also provided to control the fan 238 to be off, on for one minute and off for five minutes, and on continuously, in a toggle manner. In this regard, there are three light emitting diodes (LEDs) 260, 262 and 264 to indicate the fan settings of off, on for one minute and off for five minutes, and on continuously.

Once scent dispenser 110 is turned on, and the heat and fan settings are made, the appropriate heater assembly 172 is activated to heat the respective wick 162 and thereby vaporize the liquid fragrance. The central processing unit (CPU) is preset with the amount of time that the heater assemblies are activated, for example, four, six or eight hours, and starts the timer running. If scent dispenser 110 is turned off in the middle of a cycle, and then turned back on, the CPU calculates the remaining time in the cycle for that particular scent and activates the respective heater assembly 172 for that period of time. At the end of this period of time, this heater assembly 172 is deactivated, and the heater assembly 172 for the next fragrance is activated, whereupon the timer starts running again.

In addition, or alternatively, a fragrance selection switch can be provided, similar to that of tactile switch 100 to automatically switch over and activate the next heater assembly 172 and activate another fragrance for the start of a new time period, and thereby start the cycles running again.

It will therefore be appreciated that, in addition to the aspects of the first embodiment of scent dispenser 10, scent dispenser 110 adds the aspects of the spring biased platforms 146 which support bottles 156, the clamp housings 176 which clamp on different neck sizes, the extendable tubes 194, 196 and 198 to accommodate the different size bottles 156, the use of the gel packs 218 above the heater assemblies 172, and the fan 238 for blowing the fragrance out of scent dispenser 110.

Of course, it will be appreciated that the gel packs 218 can be used without the bottles 156, or alternatively, the bottles 156 can be used without the gel packs 218, or as a further embodiment, the gel packs 218 and bottles 156 can be used together in combination. Thus, for example, two bottles 156 and one gel pack 218 can be used.

Having described specific preferred embodiments of the invention with reference to the accompanying drawings, it will be appreciated that the present invention is not limited to those precise embodiments and that various changes and modifications can be effected therein by one of ordinary skill in the art without departing from the scope or spirit of the invention as defined by the appended claims.

What is claimed is:

1. A multi-fragrance scent dispenser comprising:
    a housing having an outlet opening;
    a first heater;
    a second heater;
    a first holder in the housing for adjustably holding a first liquid fragrance container having a first wick extending out of the first liquid fragrance container at a desired height such that the first wick is surrounded by the first heater when said first liquid fragrance container is held by said first holder;
    a second holder in the housing for adjustably holding a first liquid fragrance container having a second wick extending out of the second liquid fragrance container at a desired height such that the second wick is surrounded by the second heater when said second liquid fragrance container is held by said second holder; and
    a control circuit for selectively controlling activation of said first and second heaters.

2. A multi-fragrance scent dispenser according to claim 1, wherein each said holder includes an adjustable platform for supporting said respective liquid fragrance container at a plurality of different heights.

3. A multi-fragrance scent dispenser according to claim 2, wherein each said holder includes a spring for biasing the respective platform in a direction toward the respective heater, and a limit for limiting movement of each platform in said direction.

4. A multi-fragrance scent dispenser according to claim 1, wherein each said holder includes a clamp for clamping a neck of the respective container.

5. A multi-fragrance scent dispenser according to claim 4, further comprising:
    a support for holding each said heater at a respective position, and
    a connecting assembly for connecting said clamp to said support.

6. A multi-fragrance scent dispenser according to claim 5, wherein said connecting assembly includes a plurality of telescoping tubes which enables said clamp to move toward and away from the respective heater.

7. A multi-fragrance scent dispenser according to claim 6, wherein said telescoping tubes are held in desired positions relative to each other by friction.

8. A multi-fragrance scent dispenser according to claim 4, wherein each said clamp includes an adjustable clamping mechanism for clamping onto necks having different diameters.

9. A multi-fragrance scent dispenser according to claim 8, wherein said adjustable clamping mechanism includes:
    a clamp housing,
    two scissor arms mounted in said clamp housing, each having an arcuate holding section,
    a spring assembly for normally biasing said scissor arms toward each other to clamp around the neck of a container, and
    extensions of said scissor arms for grasping in order to move said arcuate holder sections away from each other against the force of said spring assembly.

10. A multi-fragrance scent dispenser according to claim 1, further comprising a gel pack holder mounted immediately above each said heater for holding a fragrance gel pack which emits a fragrance when heated by the respective heater.

11. A multi-fragrance scent dispenser according to claim 10, wherein said gel pack holder includes a plurality of openings for emission of the vaporized gel fragrance to the outlet opening in the housing.

12. A multi-fragrance scent dispenser according to claim 1, further comprising a fan in the housing for blowing the vaporized fragrance to the outlet opening in the housing.

13. A multi-fragrance scent dispenser according to claim 1, wherein the housing includes:
    a base including the first heater; second heater; first holder; second holder; and control circuit; and
    a cover for covering the base and including the outlet opening.

14. A multi-fragrance scent dispenser according to claim 1, further comprising at least one additional heater, and at least one additional holder in the housing for adjustably holding at least one additional liquid fragrance container having a wick extending therefrom, at a desired height such that the respective wick thereof is surrounded by the at least one additional heater when said at least one liquid fragrance container is held by said at least one additional holder.

* * * * *